United States Patent
Park et al.

(10) Patent No.: US 9,987,187 B2
(45) Date of Patent: Jun. 5, 2018

(54) APPARATUS AND METHOD FOR CONTROLLING SMART WEAR

(71) Applicant: ELECTRONICS AND TELECOMMUNICATIONS RESEARCH INSTITUTE, Daejeon (KR)

(72) Inventors: Hyung-Il Park, Daejeon (KR); Byoung-Gun Choi, Daejeon (KR); Sung-Weon Kang, Daejeon (KR); Chang-Hee Hyoung, Daejeon (KR); In-Gi Lim, Daejeon (KR); Tae-Wook Kang, Daejeon (KR); Jung-Hwan Hwang, Daejeon (KR); Kyung-Soo Kim, Daejeon (KR); Jung-Bum Kim, Daejeon (KR); Sung-Eun Kim, Daejeon (KR); Kyung-Hwan Park, Daejeon (KR); Tae-Young Kang, Seoul (KR)

(73) Assignee: ELECTRONICS AND TELECOMMUNICATIONS RESEARCH INSTITUTE, Daejeon (KR)

(*) Notice: Subject to any disclaimer, the term of this patent is extended or adjusted under 35 U.S.C. 154(b) by 389 days.

(21) Appl. No.: 14/162,294

(22) Filed: Jan. 23, 2014

(65) Prior Publication Data
US 2014/0303529 A1 Oct. 9, 2014

(30) Foreign Application Priority Data
Apr. 3, 2013 (KR) .................. 10-2013-0036485

(51) Int. Cl.
*A61H 1/02* (2006.01)
*A61H 3/00* (2006.01)
(Continued)

(52) U.S. Cl.
CPC .............. *A61H 1/0218* (2013.01); *A61B 5/11* (2013.01); *A61B 5/6804* (2013.01); *A61H 3/00* (2013.01);
(Continued)

(58) Field of Classification Search
CPC ................................................ G09B 19/0038
(Continued)

(56) References Cited

U.S. PATENT DOCUMENTS 5,662,693 A * 9/1997 Johnson ..................... A61F 5/01
607/48
5,919,149 A * 7/1999 Allum ..................... A61B 5/1116
600/595
(Continued)

FOREIGN PATENT DOCUMENTS

KR 10-2009-0105785 10/2009

*Primary Examiner* — Robert J Utama
(74) *Attorney, Agent, or Firm* — Kile Park Reed & Houtteman PLLC

(57) ABSTRACT

Disclosed herein are an apparatus and method for controlling smart wear. The apparatus for controlling smart wear includes a motion capture unit, an error information unit, a motion estimation unit, and an actuation unit. The motion capture unit captures a motion of a user using sensors included in the smart wear. Then error information unit generates user error information using reference motion information and the results of the motion capture. The motion estimation unit estimates a subsequent motion of the user using the user error information. The actuation unit controls the smart wear of the user in real time using the estimated subsequent motion and the user error information.

7 Claims, 4 Drawing Sheets

(51) Int. Cl.
　　　*G06K 9/00*　　　(2006.01)
　　　*A61B 5/11*　　　(2006.01)
　　　*A61B 5/00*　　　(2006.01)
(52) U.S. Cl.
　　　CPC ...... *G06K 9/00342* (2013.01); *A61B 2505/09* (2013.01); *A61H 2201/1207* (2013.01); *A61H 2201/165* (2013.01); *A61H 2201/5007* (2013.01); *A61H 2201/5069* (2013.01); *A61H 2201/5071* (2013.01); *A61H 2201/5079* (2013.01); *A61H 2201/5084* (2013.01); *A61H 2201/5092* (2013.01)
(58) Field of Classification Search
　　　USPC .......................................................... 434/258
　　　See application file for complete search history.

(56) References Cited

U.S. PATENT DOCUMENTS

| | | | |
|---|---|---|---|
| 6,113,395 A | 9/2000 | Hon | |
| 6,369,834 B1 | 4/2002 | Zilles et al. | |
| 7,190,141 B1* | 3/2007 | Ashrafiuon | B25J 9/0006 318/568.12 |
| 7,292,151 B2* | 11/2007 | Ferguson | A61B 5/4023 340/407.1 |
| 2003/0120183 A1* | 6/2003 | Simmons | A61F 4/00 600/595 |
| 2007/0100666 A1* | 5/2007 | Stivoric | G01R 29/0814 705/3 |
| 2007/0123997 A1* | 5/2007 | Herr | A61F 2/60 623/27 |
| 2008/0009771 A1* | 1/2008 | Perry | B25J 9/0006 600/587 |
| 2010/0113980 A1* | 5/2010 | Herr | A61F 2/60 600/587 |
| 2010/0114329 A1* | 5/2010 | Casler | B25J 19/0008 623/24 |
| 2011/0006926 A1 | 1/2011 | Kim et al. | |
| 2011/0166491 A1* | 7/2011 | Sankai | A41D 13/1281 601/84 |
| 2012/0330198 A1* | 12/2012 | Patoglu | B25J 9/0006 601/33 |
| 2013/0110266 A1* | 5/2013 | Snaterse | A63B 69/0028 700/91 |
| 2014/0172166 A1* | 6/2014 | Kim | B25J 3/04 700/259 |
| 2014/0221894 A1* | 8/2014 | Nagasaka | A61H 3/00 602/23 |
| 2016/0202755 A1* | 7/2016 | Connor | A61B 5/1126 73/865.4 |
| 2017/0203432 A1* | 7/2017 | Andrianesis | B25J 9/0006 |

\* cited by examiner

APPARATUS AND METHOD FOR CONTROLLING SMART WEAR

CROSS REFERENCE TO RELATED APPLICATION

This application claims the benefit of Korean Patent Application No. 10-2013-0036485, filed on Apr. 3, 2013, which is hereby incorporated by reference in its entirety into this application.

BACKGROUND OF THE INVENTION

1. Technical Field

The present invention relates generally to an apparatus and method for controlling smart wear and, more particularly, to a smart wear apparatus and method that are capable of converting standard motion information for rehabilitation training or posture correction in accordance with a user and providing the user with optimized motion information corresponding to the results of the conversion, thereby controlling a rehabilitation motion or posture of the user in real time.

2. Description of the Related Art

Motion capturing technology has been chiefly applied to virtual reality via 3-D animation or computer graphics, and is used to produce images.

Motion manipulation technology has been chiefly applied to robotics, computer graphics, or virtual reality, and has been sometimes applied to applications for some rehabilitants.

In general, after a motion has been captured, a rehabilitation therapist or a coach describes and then instructs a rehabilitant or a trainee on the correction. In this case, training time is likely to increase because there is a difference between the understanding and behavior of the rehabilitant or trainee.

A system was proposed that put an expert's motion or posture regarding content to be taught to a database, compared the expert's motion or posture with a motion or posture of a user, and provided notification of the difference between the expert's motion or posture motion with the motion or posture of the user.

Korean Patent No. 1087135 entitled "Teaching Apparatus and Method based on Motion Content" discloses a method of prompting a user to make a specific motion by causing the user to apply calculated force based on motion content.

However, the conventional technology is problematic in that it is difficult to overcome the differences between the genders, ages and body conditions of individual users and then construct target databases suitable for the individual users.

SUMMARY OF THE INVENTION

Accordingly, the present invention has been made keeping in mind the above problems occurring in the prior art, and an object of the present invention is to provide a smart wear apparatus and method that are capable of converting standard motion information for rehabilitation training or posture correction in accordance with a user and providing the user with optimized motion information corresponding to the results of the conversion, thereby controlling a rehabilitation motion or posture of the user in real time.

In accordance with an aspect of the present invention, there is provided a method of controlling smart wear, including capturing, by an apparatus for controlling the smart wear, a motion of a user using sensors included in the smart wear; generating user error information using reference motion information and results of the motion capture; estimating a subsequent motion of the user using the user error information; and controlling the smart wear of the user in real time using the estimated subsequent motion and the user error information.

The method of claim may further including, before generating the user error information, selecting standard motion information corresponding to a final target model of rehabilitation training or posture correction; converting the standard motion information in accordance with the smart wear; and generating the reference motion information by applying user information to the converted standard motion information.

The user information may include physical information, such as a gender, age and height of the user, and competence level information corresponding to the standard motion information.

Controlling the smart wear of the user in real time may include generating a motion control signal capable of controlling an error in the motion of the user using the estimated subsequent motion and the user error information; and controlling the smart wear by feeding back the error in the motion of the user in real time using the motion control signal.

Controlling the smart wear of the user in real time may include controlling at least one actuator attached to the smart wear using the motion control signal.

In accordance with another aspect of the present invention, there is provided an apparatus for controlling smart wear, including a motion capture unit configured to capture a motion of a user using sensors included in the smart wear; an error information unit configured to generate user error information using reference motion information and results of the motion capture; a motion estimation unit configured to estimate a subsequent motion of the user using the user error information; and an actuation unit configured to control the smart wear of the user in real time using the estimated subsequent motion and the user error information.

The apparatus may further include a standard information unit configured to select standard motion information corresponding to a final target model of rehabilitation training or posture correction; an information conversion unit configured to convert the standard motion information in accordance with the smart wear; and an optimized information generation unit configured to generate the reference motion information by applying user information to the converted standard motion information.

The information conversion unit may include a setup condition unit configured to define setup conditions including locations and a number of sensors and actuators within the smart wear; a selection unit configured to select additional information to be added to the standard motion information; and an output unit configured to add the selected additional information to the standard motion information and then output the standard motion information with the additional information added, or to output the standard motion information without the additional information.

The additional information may include at least one of joint angles, sensor coordinate values, angular speed values, and a sampling cycle corresponding to the final target model.

The sensors may correspond to at least one of optical sensors, acceleration sensors, gyro sensors, terrestrial magnetism sensors, and pressure sensors.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
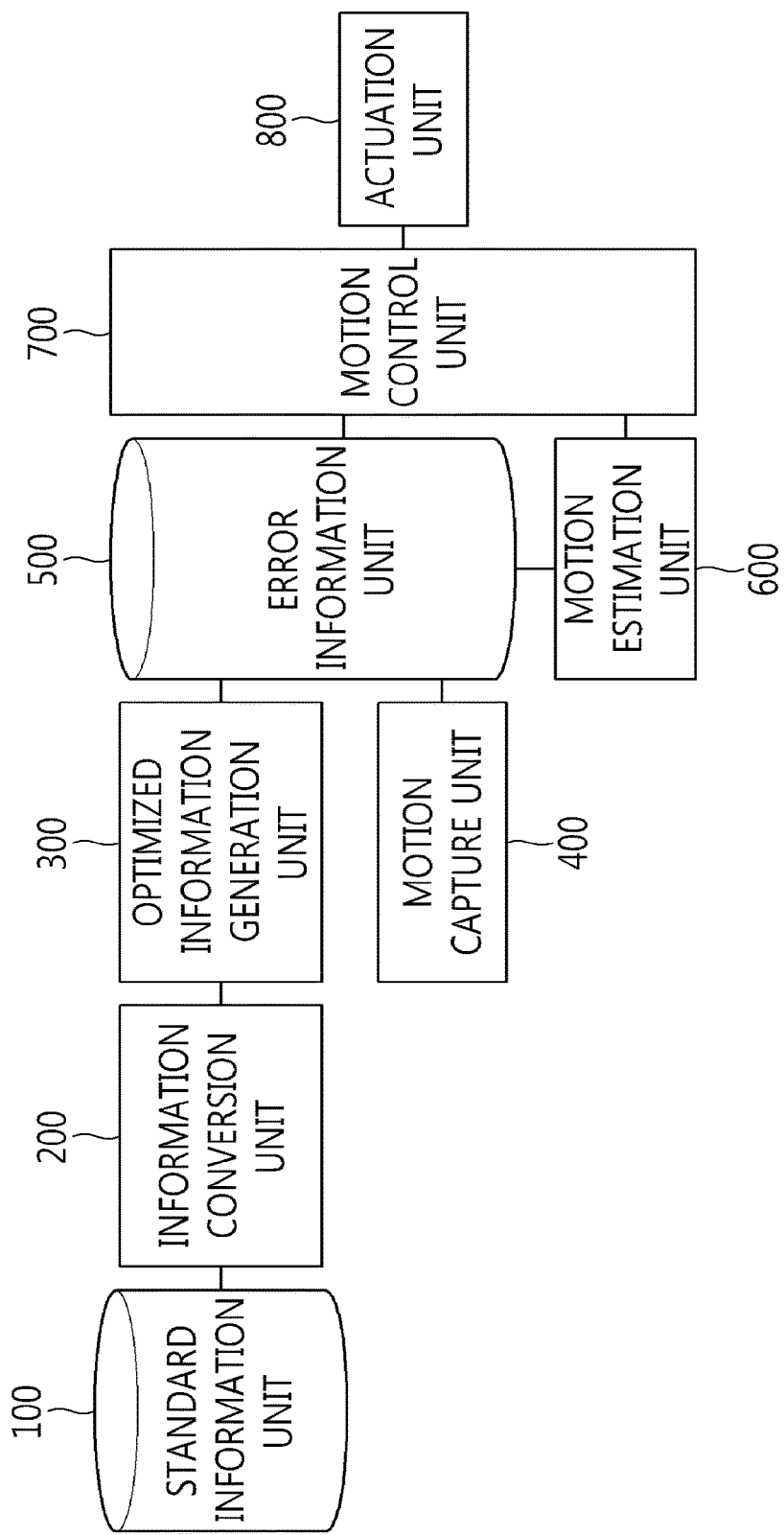
FIG. 1 is a configuration diagram schematically illustrating an apparatus for controlling smart wear according to an embodiment of the present invention.

The present invention will be described in detail below with reference to the accompanying drawings. Repeated descriptions and descriptions of known functions and configurations which have been deemed to make the gist of the present invention unnecessarily vague will be omitted below. The embodiments of the present invention are intended to fully describe the present invention to a person having ordinary knowledge in the art. Accordingly, the shapes, sizes, etc. of elements in the drawings may be exaggerated to make the description clear.

In the fields of rehabilitation and sports in which users should be trained in using their bodies, rehabilitation training and posture correction regarding motions and postures is a continuation of mundane processes that require a lot of time.

The present invention provides an apparatus and method for controlling smart wear that are capable of checking and correcting a motion of a user in real time through the convergence of IT and functional fiber.

An apparatus and method for controlling smart wear according to embodiments of the present invention will be described below with reference to the accompanying drawings.

Figure 2:
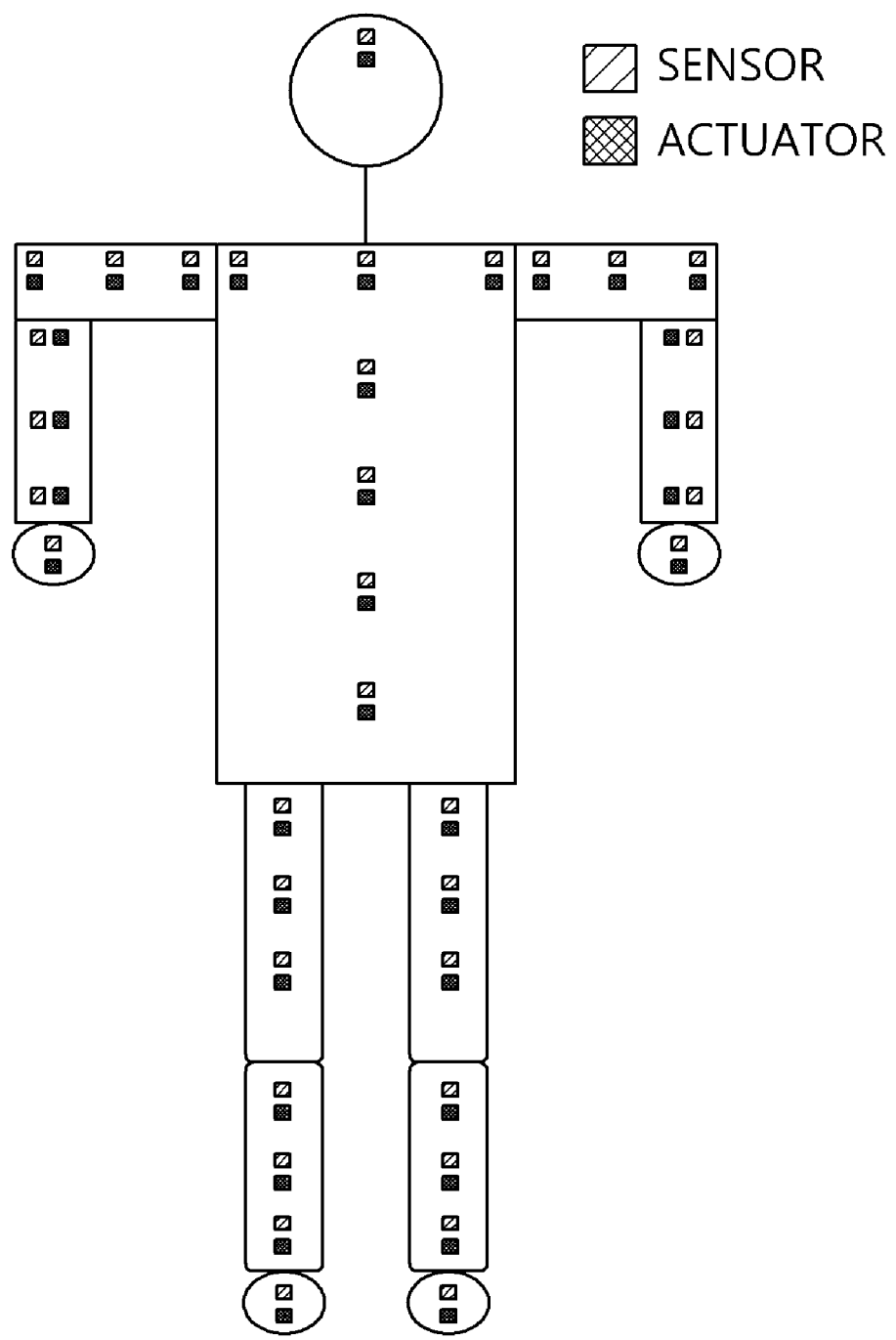
FIG. 2 is a reference diagram illustrating the application of the apparatus for controlling smart wear according to the embodiment of the present invention to a user.

FIG. 1 is a configuration diagram schematically illustrating an apparatus for controlling smart wear according to an embodiment of the present invention, and FIG. 2 is a reference diagram illustrating the application of the apparatus for controlling smart wear according to the embodiment of the present invention to a user.

Smart wear corresponds to future clothing in which digital sensors, microcomputer chips, etc. are attached to a high-functional fabric and which is capable of sensing and reacting to external stimuli.

The apparatus for controlling smart wear according to an embodiment of the present invention checks a motion of a user in real time and then corrects the motion of the user using the smart wear in the field of rehabilitation training or posture correction in which the user should be trained in using his or her body. If the apparatus for controlling smart wear is applied to a user, it is assumed that sensors and actuators included in smart wear are provided to the user.

Referring to FIG. 1, the apparatus for controlling smart wear includes a standard information unit 100, an information conversion unit 200, an optimized information generation unit 300, a motion capture unit 400, an error information unit 500, a motion estimation unit 600, a motion control unit 700, and an actuation unit 800.

The standard information unit 100 includes information about the final target model of rehabilitation training or posture correction, that is, standard motion information. The standard motion information may correspond, for example, to a posture of a professional player in the field of sports and to the movable articulation exercise range of a normal person in the field of rehabilitation.

The information conversion unit 200 converts standard motion information included in the standard information unit 100 in response to actuators and sensors included in smart wear, or applies additional information to the standard motion information.

The optimized information generation unit 300 generates optimized motion information by applying physical information, such as a user's gender, age and height, and competence level information to the standard motion information converted by the information conversion unit 200.

The motion capture unit 400 captures a motion of a user, for example, a trainee or a rehabilitant. For this purpose, the motion capture unit 400 may capture a motion using sensors attached to smart wear, for example, an optical sensor, an acceleration sensor, a gyro sensor, a terrestrial magnetism sensor, and a pressure sensor, as illustrated in FIG. 2.

The error information unit 500 compares motion information optimized by the optimized information generation unit 300 with the results of the user motion captured by the motion capture unit 400, that is, capture results, and generates user error information corresponding to the results of the comparison. The user error information refers to the difference between the user motion and the optimized motion information, which is obtained by comparing the optimized motion information provided to the user with the captured user motion, that is, an erroneous motion.

Furthermore, the error information unit 500 stores the generated user error information.

The motion estimation unit 600 estimates a subsequent motion of the user using the user error information stored in the error information unit 500.

The apparatus for controlling smart wear according to the embodiment of the present invention may previously correct an error in an estimated subsequent motion by estimating a subsequent motion of a user, as in the motion estimation unit 600.

If a motion of a user is excessively slow or fast, the motion estimation unit 600 may not compare optimized motion information with capture results, but the present invention is not limited thereto.

The motion control unit 700 generates a motion control signal capable of controlling an error in the motion of the user in real time using the subsequent motion of the user estimated by the motion estimation unit 600 and the user error information stored in the error information unit 500. The motion control signal includes a function of controlling actuation corresponding to the user error information and a function of controlling the priority of an error in a motion of a user based on expert knowledge.

The actuation unit 800 controls a motion of a user, that is, smart wear that is worn by the user, by feeding back an error in the motion of the user in real time using a motion control signal generated by the motion control unit 700. For this purpose, the actuation unit 800 includes at least one actuator. As illustrated in FIG. 2, the actuation unit 800 may construct various types of profiles that are suitable for the perception and sensation cognition abilities of body portions to which at least one actuator may be attached. In this case, each of the profiles may include the frequency, strength and length cycle of a motion.

The actuator according to an embodiment of the present invention may be a cylinder- or pancake-type linear motor that may be attached to a fabric, or a fabric-type actuator, such as a polyvinylidene fluoride (PVDF) actuator, that is, an electroactive polymer-type actuator. However, the present invention is not limited thereto.

The information conversion unit 200 of the apparatus for controlling smart wear will be described in detail below with reference to FIG. 3.

Figure 3:
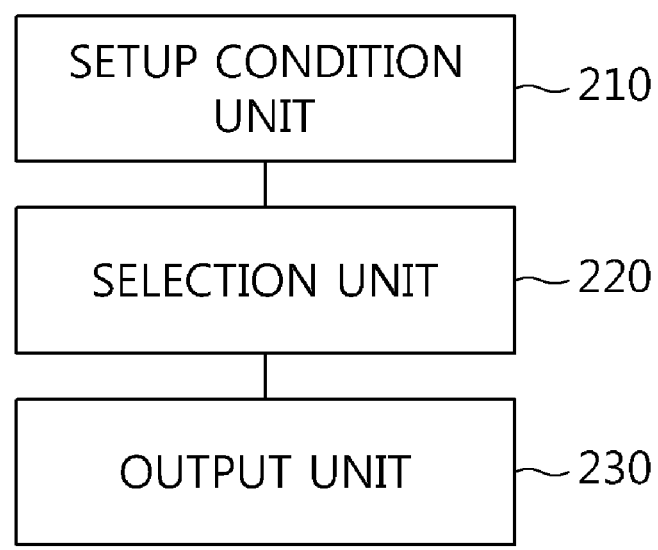
FIG. 3 is a configuration diagram illustrating the information conversion unit of the apparatus for controlling smart wear according to an embodiment of the present invention.

FIG. 3 is a configuration diagram illustrating the information conversion unit 200 of the apparatus for controlling smart wear according to an embodiment of the present invention.

First, the information conversion unit 200 converts standard motion information included in the standard information unit 100 in accordance with actuators and sensors included in smart wear, or applies additional information to the standard motion information.

Referring to FIG. 3, the information conversion unit 200 includes a setup condition unit 210, a selection unit 220, and an output unit 230.

The setup condition unit 210 defines setup conditions that include the locations of sensors and actuators included within smart wear, as illustrated in FIG. 2, and the numbers of sensors and actuators attached to a fabric.

The selection unit 220 selects additional information to be added to standard motion information. In this case, the additional information includes joint angles, sensor coordinate values, angular speed values, and a sampling cycle.

The output unit 230 adds additional information selected by the selection unit 220 to standard motion information and outputs the standard motion information with additional information added thereto, or outputs standard motion information without additional information.

A method of controlling smart wear will be described in detail below with reference to FIG. 4.

Figure 4:
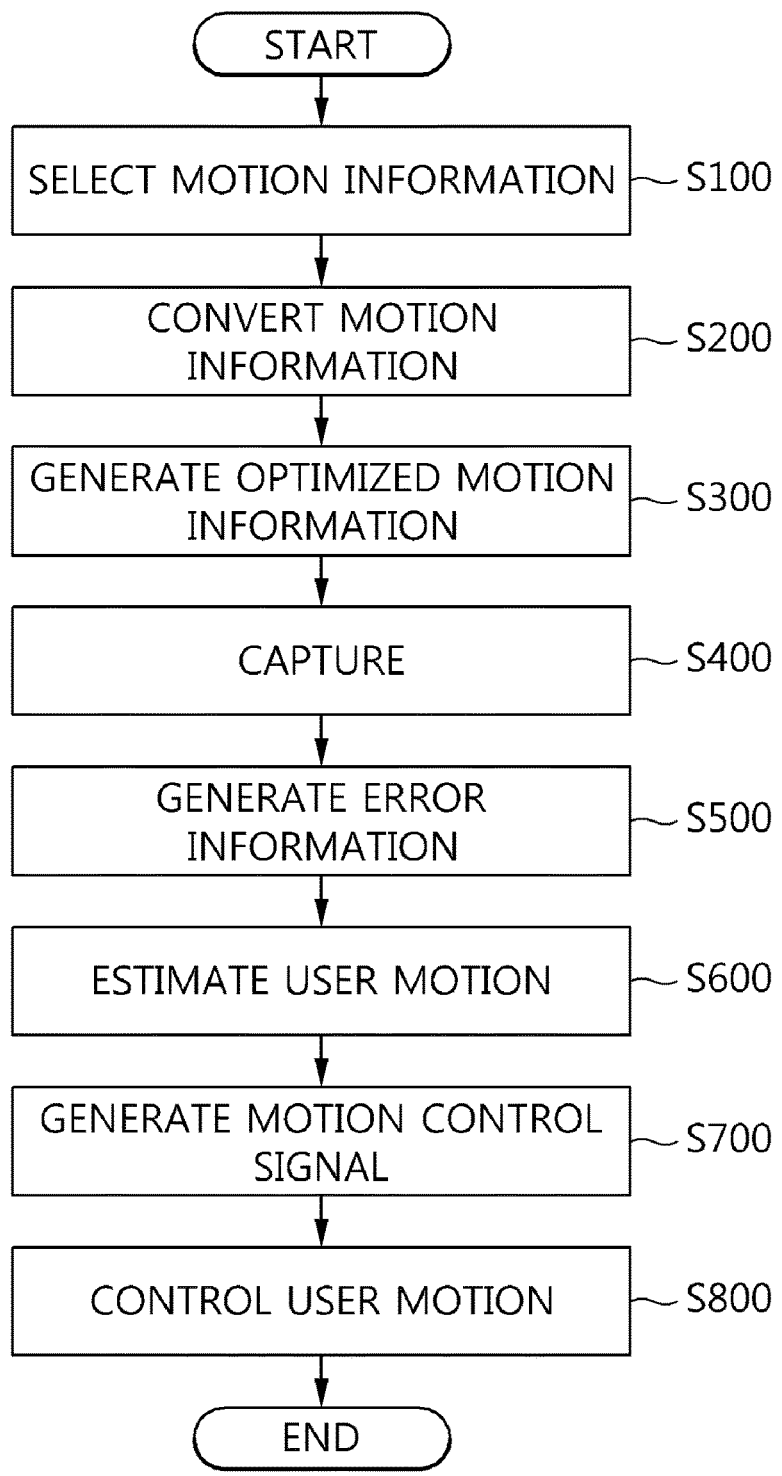
FIG. 4 is a flowchart illustrating a method of controlling smart wear according to an embodiment of the present invention.

FIG. 4 is a flowchart illustrating a method of controlling smart wear according to an embodiment of the present invention.

Referring to FIG. 4, the apparatus for controlling smart wear selects information corresponding to the final target model of rehabilitation training or posture correction, that is, standard motion information at step S100. The standard motion information may be, for example, a posture of a professional player in the field of sports and the movable articulation exercise range of a normal person in the field of rehabilitation.

The apparatus for controlling smart wear converts the standard motion information in response to actuators and sensors included in smart wear, or applies additional information to the standard motion information at step S200.

At step S300, the apparatus for controlling smart wear generates optimized motion information by applying user information to the standard motion information converted at step S200. The user information includes physical information, such as the gender, age and height of the user, and user competence level information.

The apparatus for controlling smart wear captures a motion of the user, such as a trainee or a rehabilitant, using sensors included in the smart wear at step S400. In this case, the smart wear corresponds to clothing worn by the user, and the sensors included in the smart wear may be optical sensors, acceleration sensors, gyro sensors, terrestrial magnetism sensors, or pressure sensors. Furthermore, the optimized motion information corresponds to reference motion information that is required to generate the user error information through comparison with the capture results of step S400.

The apparatus for controlling smart wear compares the optimized motion information generated at step S300 with the capture results obtained at step S400 and generates the user error information corresponding to the results of the comparison at step S500. The user error information is information corresponding to the difference between the user motion and the optimized motion information, and is information required to correct the motion of the user based on the optimized motion information.

At step S600, the apparatus for controlling smart wear estimates a subsequent motion of the user using the user error information generated at step S500.

At step S700, the apparatus for controlling smart wear generates a motion control signal capable of controlling an error in the motion of the user in real time using the subsequent motion of the user estimated at step S600 and the user error information generated at step S500. The motion control signal includes a function of controlling actuation corresponding to the user error information and a function of controlling the priority of an error in the motion of the user based on expert knowledge.

At step S800, the apparatus for controlling smart wear controls the motion of the user, that is, smart wear that is worn by the user, by feeding back an error in the motion of the user in real time using the motion control signal generated at step S700. At step S800, the apparatus for controlling smart wear may construct various types of profiles that are suitable for the perception and sensation cognition abilities of body portions to which at least one actuator may be attached. Each of the profile may include the frequency, strength and length cycle of a motion.

As described above, the apparatus and method for controlling smart wear according to an embodiment of the present invention can convert standard motion information for rehabilitation training or posture correction in accordance with a user, and can provide the user with optimized motion information corresponding to the results of the conversion, thereby controlling the rehabilitation motion or posture of the user in real time.

Furthermore, the apparatus and method for controlling smart wear according to an embodiment of the present invention can predict a motion of a user, so that the user can make a rehabilitation motion or assume an accurate posture through faster feedback even in the absence of a rehabilitation therapist or a coach, thereby helping both the rehabilitation therapist or coach and the rehabilitant or trainee.

Moreover, the apparatus and method for controlling smart wear according to an embodiment of the present invention can correct a motion in real time when a user makes the motion, and can receive faster feedback through motion prediction. Accordingly, a rehabilitation therapist or a coach can take care of many rehabilitants or trainees, and a rehabilitant or a trainee can increase the accuracy of training or correction by overcoming the limitations of post-correction, can reduce time, efforts and cost, and can perform more precise rehabilitation or correction while overcoming the limitations of correction based on the point of view of a rehabilitation therapist or a coach.

Although the preferred embodiments of the present invention have been disclosed for illustrative purposes, those skilled in the art will appreciate that various modifications, additions and substitutions are possible without departing from the scope and spirit of the invention as disclosed in the accompanying claims.

What is claimed is:

1. A method of controlling smart wear, comprising: selecting standard motion information corresponding to a final target model of rehabilitation training or posture correction;
defining setup conditions which include locations and a number of sensors and actuators included within the smart wear;
converting the standard motion information in accordance with the setup conditions of the smart wear, wherein said conversion comprises selecting additional information to be added to the standard motion information in accordance with the setup conditions, said angular speed values, and a sampling cycle corresponding to the final target model;
generating optimized motion information by applying user information of a user to the converted standard motion information, the user information comprises physical information selected from the group of gender, age and height of the user, and competence level information corresponding to the standard motion information;
capturing, motion of the user using sensors included in the smart wear;
comparing the optimized motion information and results of the motion capture to obtain a difference between the results of the motion capture and the optimized motion information;
generating user error information corresponding to the difference between the results of the motion capture and the optimized motion information;
estimating a subsequent motion of the user using the user error information; and controlling the smart wear of the user in real time using the estimated subsequent motion and the user error information.

2. The method of claim 1, wherein controlling the smart wear of the user in real time comprises:
generating a motion control signal capable of controlling an error in the motion of the user using the estimated subsequent motion and the user error information; and
controlling the smart wear by feeding back the error in the motion of the user in real time using the motion control signal.

3. The method of claim 2, wherein controlling the smart wear of the user in real time comprises controlling the at least one actuator.

4. An apparatus for controlling smart wear, comprising:
a standard information unit that selects standard motion information corresponding to a final target model of rehabilitation training or posture correction;
an information conversion unit that receives the standard motion information from the standard information unit to define setup conditions which include locations and a number of sensors and actuators included within the smart wear and converts the standard motion information in accordance with the setup conditions of the smart wear, wherein said conversion comprises selecting additional information to be added to the standard motion information in accordance with the setup conditions, said additional information comprising at least one of joint, angles, sensor coordinate values, angular speed values, and a sampling cycle corresponding to the final target model;
an optimized information generation unit that receives the converted standard motion information from the information conversion unit to generate optimized motion information by applying user information of a user to the converted standard motion information, the user information comprises physical information selected from the group of gender, age and height of the user, and competence level information corresponding to the standard motion information;
a motion capture unit that captures a motion of the user using sensors included in the smart wear;
an error information unit that receives the optimized motion information from the optimized information generation unit and results of the motion capture from the motion capture unit to compare the optimized motion information and the results of the motion capture to obtain a difference between the results of the motion capture and the optimized motion information and generates user error information corresponding to the difference between the results of the motion capture and the optimized motion information;
a motion estimation unit that receives the user error information from the error information unit to estimate a subsequent motion of the user using the user error information; and
an actuation unit that receives the estimated subsequent motion from the motion estimation unit and the user error information from the error information unit to generate a motion control signal capable, of controlling the smart wear of the user in real time using the estimated subsequent motion and the user error information.

5. The apparatus of claim 4, wherein the information conversion unit comprises:
a setup condition unit that defines the setup conditions;
a selection unit that receives the setup conditions from the setup condition unit to select the additional information to be added to the standard motion information; and
an output unit that receives the selected additional information from the selection unit to add the selected additional information to the standard motion information and then outputs the standard motion information with the additional information added, or outputs the standard motion information without the additional information.

6. The apparatus of claim 5, wherein the sensors correspond to at least one of optical sensors, acceleration sensors, gyro sensors, terrestrial magnetism sensors, and pressure sensors.

7. The method of claim 1, wherein the converting the standard motion information in accordance with setup conditions of the smart wear further comprises:
selecting the additional information to be added to the standard motion information; and
adding the selected additional information to the standard motion information and then outputting the standard motion information with the additional information added, or outputting the standard motion information without the additional information.

* * * * *